(12) United States Patent
Mueller (10) Patent No.: US 9,851,301 B2
(45) Date of Patent: Dec. 26, 2017

(54) METHOD AND DEVICE FOR RECOGNIZING A MIXED OR UNMIXED STATE OF A SAMPLE

(71) Applicant: Roche Diagnostics Operations, Inc., Indianapolis, IN (US)

(72) Inventor: Steffen Mueller, Heilbronn (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 113 days.

(21) Appl. No.: 15/081,361

(22) Filed: Mar. 25, 2016

(65) Prior Publication Data

US 2016/0209329 A1 Jul. 21, 2016

Related U.S. Application Data

(63) Continuation of application No. PCT/EP2014/071061, filed on Oct. 1, 2014.

(30) Foreign Application Priority Data

Oct. 1, 2013 (DE) .................. 10 2013 219 972

(51) Int. Cl.
| | |
|---|---|
| *G01N 21/59* | (2006.01) |
| *G01N 33/49* | (2006.01) |
| *G01N 15/04* | (2006.01) |
| *G01N 21/31* | (2006.01) |
| *B01L 3/00* | (2006.01) |
| *G01N 35/00* | (2006.01) |
| *G01N 21/84* | (2006.01) |

(52) U.S. Cl.
CPC ........... *G01N 21/59* (2013.01); *G01N 15/042* (2013.01); *G01N 33/49* (2013.01); *G01N 33/491* (2013.01); *G01N 35/0099* (2013.01); *B01L 3/5021* (2013.01); *G01N 21/3151* (2013.01); *G01N 2015/045* (2013.01); *G01N 2021/8405* (2013.01); *G01N 2035/00495* (2013.01)

(58) Field of Classification Search
CPC .... G01N 21/59; G01N 35/0099; G01N 33/49; G01N 15/042; G01N 33/491; G01N 2021/8405; G01N 2035/00495; G01N 2015/045; G01N 21/3151; G01N 15/05; G01N 33/48; B01L 3/5021; B01L 3/50215; B01L 3/5082
See application file for complete search history.

(56) References Cited

U.S. PATENT DOCUMENTS

| 5,309,216 A | * | 5/1994 | Weichert ................ G01N 15/02 356/335 |
|---|---|---|---|
| 6,770,883 B2 | | 8/2004 | McNeal et al. |

(Continued)

FOREIGN PATENT DOCUMENTS

| CA | 2244397 A1 | 2/1999 |
|---|---|---|
| CN | 102455281 A | 5/2012 |

(Continued)

*Primary Examiner* — Michael P Lapage
(74) *Attorney, Agent, or Firm* — Roche Diagnostics Operations, Inc.

(57) ABSTRACT

A method for automated identification of a state of a sample such as, for example, for identifying whether or not the sample was centrifuged is presented. A device for analyzing samples and a laboratory automation system are also presented in which the method is applied.

13 Claims, 2 Drawing Sheets

(56) References Cited

U.S. PATENT DOCUMENTS

| | | | |
|---|---|---|---|
| 7,141,213 B1 | 11/2006 | Pang et al. | |
| 7,227,622 B2 | 6/2007 | Itoh | |
| 7,473,897 B2* | 1/2009 | Braendle | G01F 23/2927 |
| | | | 250/343 |
| 7,771,659 B2 | 8/2010 | Ziegler | |
| 2004/0219266 A1* | 11/2004 | Milliken | G01N 21/274 |
| | | | 426/231 |
| 2005/0101028 A1* | 5/2005 | Kawamura | B01F 5/0206 |
| | | | 436/164 |
| 2012/0003659 A1* | 1/2012 | Yoo | G01N 21/07 |
| | | | 435/6.12 |
| 2012/0013889 A1 | 1/2012 | Heise | |
| 2013/0258336 A1* | 10/2013 | Ostermeyer | G01N 21/59 |
| | | | 356/364 |

FOREIGN PATENT DOCUMENTS

| | | |
|---|---|---|
| CN | 102519881 A | 6/2012 |
| WO | 2003/060484 A1 | 7/2003 |
| WO | 2005/003738 A2 | 1/2005 |
| WO | 2006/037941 A1 | 4/2006 |
| WO | 2008/069720 A1 | 6/2008 |
| WO | 2009/079067 A1 | 6/2009 |
| WO | 2010/129779 A1 | 11/2010 |
| WO | 2011/019576 A1 | 2/2011 |
| WO | 2012/010787 A1 | 1/2012 |
| WO | 2013/070754 A1 | 5/2013 |

* cited by examiner

METHOD AND DEVICE FOR RECOGNIZING A MIXED OR UNMIXED STATE OF A SAMPLE

CROSS-REFERENCE TO RELATED APPLICATIONS

This application is a continuation of PCT/EP2014/071061, filed Oct. 1, 2014, which is based on and claims priority to DE 10 2013 219 972.4, filed Oct. 1, 2013, which is hereby incorporated by reference.

BACKGROUND

The present disclosure relates to a method for identifying a state of a sample such as, for example, a blood sample, which is in a sample tube extending along a longitudinal direction, from a predetermined set of states, wherein the set of states contains an unmixed state and a mixed state.

Samples such as, for example, medical samples such as blood samples, are often filled into conventional sample tubes for the purposes of being subjected to analyses. By way of example, the presence of a disease, or an alcohol concentration, in the blood can be determined within the scope of such an analysis. Typically, many analyses require individual constituents of such a sample to be split prior to the analysis. In the process, a plurality of phases of different phase types is typically produced in the sample tube.

By way of example, the following phases, more precisely types of phases, are known in blood samples:

Air: a region, typically at the upper end of the sample tube that has not been filled by liquid or solid constituents;

Whole blood: blood with all constituents that has not been separated, as taken from a human or an animal;

Blood plasma or serum: a liquid component of the blood, remaining as a supernatant when the cellular constituents were separated from a blood sample;

Coagulum: cellular constituents of blood such as red blood cells, blood platelets and white blood cells; and/or Gel: a substance which is largely transparent in the visible spectrum, introduced into the sample tube in addition to the blood sample in order to improve the separation. The gel is typically already filled into the sample tube by the manufacturer of the sample tube and is therefore situated at the lower edge or end of the sample tube prior to the separation steps possibly to be carried out.

After a sample tube is filled with a blood sample, the sample is initially in a mixed state, in which all constituents of the human or animal blood are contained in a single homogeneous phase. This applies at least for as long as there has not been an onset of any significant blood sedimentation. Now, prior to the analysis, the sample is intended to be transferred into an unmixed state, in which the individual constituents of the blood are present in separated phases. To this end, the sample is typically centrifuged, which can be carried out by a conventional laboratory centrifuge. Hence, in this typical case, the mixed state can be referred to as non-centrifuged state and the unmixed state can be referred to as centrifuged state.

It is to be understood that the terms non-centrifuged state or centrifuged state are often used within the scope of this application, as the method of centrifuging is the most common method for separating a sample. However, in principle, different separation methods can also be applied, and the results of these separation methods should also be comprised by the term centrifuged state. Likewise, the term non-centrifuged state should, in principle, denote a state in which a sample is without an actively performed separation step, independently of the envisaged separation method.

If an analysis to be performed on the sample requires an unmixed state, the analysis of a sample in the mixed state would lead, at least, to a distorted result of the analysis. Moreover, blockages of the lines or damage to the analysis instrument may be the consequence. Therefore, samples should only be analyzed in the unmixed state.

Until now, a manual check prior to the analysis step as to whether each individual sample is in the unmixed state was conventional. To this end, a human must observe each sample and identify whether the sample is in the unmixed state on the basis of the visible phase types. On the one hand, this is time-consuming and, on the other hand, there is also the risk of human failure, and so a sample in the mixed state may not be identified in good time under certain circumstances, for example, due to inattentiveness.

Therefore, there is a need for a method for identifying a state of a sample which allows an automated identification of the state as well as for a device for analyzing samples which applies such a method and a laboratory automation system with such a device.

SUMMARY

According to the present disclosure, a device, laboratory automation system and method for automated identification of a state of a sample such as a blood sample, from a predetermined set of states by the device are presented. The set of states can contain an unmixed state and a mixed state. The sample can be situated in a sample tube extending along a longitudinal direction. The method can comprise determining at least one property of the sample at a plurality of different positions along the longitudinal direction, determining at least one phase type of a phase of the sample in the sample tube on the basis of the determined property, and determining the state of the sample as a unmixed state or as a mixed state in a manner dependent on the determined phase type. At a respective position a first transmissivity of the sample across the longitudinal direction at a first wavelength can be determined as a first property and a second transmissivity of the sample across the longitudinal direction at a second wavelength can be determined as a second property during the step of determining at least one property.

Accordingly, it is a feature of the embodiments of the present disclosure to provide for a method for identifying a state of a sample which allows an automated identification of the state as well as for a device for analyzing samples which applies such a method and a laboratory automation system with such a device. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A method for automated identification of a state of a sample such as, for example, a blood sample, from a predetermined set of states by a device is presented. The set of states can contain an unmixed state and a mixed state. The sample can be situated in a sample tube extending along a longitudinal direction.

The method can comprise determining at least one property of the sample at a plurality of different positions along the longitudinal direction, determining at least one phase type of a phase of the sample in the sample tube on the basis of the determined property, and determining the state of the sample in a manner dependent on the determined phase type.

By this method, it can be possible to automate the identification, until now carried out manually, of different states of the sample, which can be in an unmixed or centrifuged state prior to an analysis step. The sources of error can be avoided. Moreover, the automation can save a significant amount of work time.

Here, for example, an automated identification can be understood to mean that a manual intervention is no longer necessary for performing the method. For example, this can be understood to mean that the result of the method, i.e. the determination of the state of the sample, does not depend on human assessment.

The sample can be a blood sample. However, this can also relate to different samples, in particular from the medical sector.

The unmixed state can be a state in which the sample can be separated into individual different phases. For example, such an unmixed state can be achieved by virtue of the sample being processed by a centrifuge, since a sample can be typically separated into individual phases of different density during centrifugation. In the example of a blood sample, the whole blood typically present prior thereto can separate into, firstly, a coagulum with the cellular constituents of the blood at the lower end of the sample tube and, secondly, the liquid blood plasma over the coagulum.

For example, a phase of the whole blood phase type cannot be separated out in a mixed state. A phase of the gel phase type being in the sample tube in addition to a phase of the whole blood phase type is not in conflict with determining a mixed state. This is because, typically, the gel can already be moved into the sample tube during the production of the sample tube and therefore can be situated at the lower end of the sample tube. If the sample tube is now filled with blood, it typically may not mix with the gel. Rather, the blood can initially remain as whole blood over the gel.

It should also be noted that whole blood can inherently carry out a certain amount of separation over time on account of natural blood sedimentation, wherein substantially blood plasma can remain at the upper end of such a phase and a phase in which the cellular constituents of the blood can more dense form below the blood plasma. The last-mentioned phase may also be referred to as pseudo-coagulum and, under certain circumstances, may not be distinguishable from a real coagulum. There is a more detailed discussion below as to how this phenomenon can be accounted for in a development of the method.

During the determination of at least one property at a respective position, it can be possible to establish at least one of a plurality of properties which can permit conclusions to be drawn about the respective phase type. To this end, a first transmissivity (or a degree of transmissivity or transmissivity factor or coefficient) of the sample across the longitudinal direction at a first wavelength can be determined as a first property at the respective position and a second transmissivity (or a degree of transmissivity or transmissivity factor or coefficient) of the sample across the longitudinal direction at a second wavelength can be determined as a second property at the respective position. Here, a transmissivity can be understood to mean a variable for the permeability of a medium for waves such as, for example, electromagnetic waves. Here, this can be the portion of electromagnetic radiation (light) which can pass through the sample and the surrounding sample tube, and possibly also through a label. In order to establish the transmissivity, the sample tube with the sample situated therein can be irradiated, for example, by light of a specific wavelength, wherein a detector lying opposite to the light source in respect of the sample tube can measure the portion of the emitted light that passed through the sample and the sample tube.

For example, the use of light with a wavelength of between 400 nm and 1200 nm for determining the first transmissivity and the use of light with a wavelength of between 1300 nm and 1700 nm for determining the second transmissivity can be suitable for the envisaged purpose in the case of a blood sample. These are values which can permit a particularly reliable distinction to be made between the phase types in question. This can be due to the fact that blood plasma, which can consist predominantly of water, can have a high first transmissivity and a low second transmissivity when the aforementioned wavelengths are used. Here, use can be made of the property of a high absorption of water in the infrared spectral range with, at the same time, a low absorption in the visible spectral range, which can occur in no other phase type typically coming into question.

Virtually no radiation can be passed at both wavelengths in the phase of the coagulum phase type, and so the transmissivity can be extremely low. In a phase of the gel phase type, a relatively high portion of the radiation can be passed at both wavelengths such that the transmissivity can be comparatively high, but lower than in the case of plasma at the first wavelength. In the phase of the whole blood phase type, only a small portion of the radiation can be passed at both wavelengths, and so the transmissivity can be comparatively low, but higher than in the case of the phase of the coagulum phase type. The described properties can allow a reliable distinction to be made between different phase types.

Transmissivity can be specified in e.g. percent. Thus, for example, a value of 80% can mean that a portion of 80% of the light radiated-in on one side of the sample tube can pass through the sample tube and the sample, whereas 20% of the light can be absorbed or reflected.

Already present transmissivity measuring methods which, for example, can conventionally serve to determine interfaces can also be used to identify the state or identify centrifugation without further outlay in terms of apparatus being required herefor.

Some embodiments of the method, by which specific phase types can be determined, are described below. It can be understood that the embodiments can be combined amongst themselves in any way such that, accordingly, more different phase types can be identified.

In accordance with one embodiment, the plasma (or serum) phase type can be determined if the first transmissivity lies above a first plasma threshold and the second transmissivity lies below a second plasma threshold. This can account for the fact that the wavelength of the light used for determining the first transmissivity can lie in a spectral region in which the plasma transmits relatively well, whereas the wavelength of the light used for determining the second transmissivity can lie in a spectral region in which the plasma transmits comparatively badly. Therefore, the first plasma threshold can have a comparatively high two-digit percentage value, while the second plasma threshold can have a relatively low value. The plasma phase type can be determined reliably by combining a high first transmissivity with a lower second transmissivity since such a combination may not occur in any other typical phase type.

It can be understood that the first transmissivity and the second transmissivity need not necessarily be evaluated separately. Rather, it can also be possible to form a quotient of the second transmissivity and the first transmissivity, wherein, in this case, it can also be possible to say that the first transmissivity can form a reference for the second transmissivity. It can be understood that the quotient or an inverse of the quotient can be used as calculation variable. The quotient can be comparatively independent of a layer thickness of a sample tube material, which can conventionally be made of transparent plastic and of a number of labels or tags stuck onto the sample tube. Hence, the quotient can allow an advantageous determination of the respective phase types.

In accordance with another embodiment, the gel phase type can be determined if the first transmissivity lies above a lower first gel threshold and below an upper first gel threshold and the second transmissivity lies above a lower second gel threshold and below an upper second gel threshold. This can account for the fact that gel can absorb the two wavelengths used for determining the first and the second transmissivity only to a very small extent. The respective lower gel thresholds can allow the gel to be distinguished from the phase types such as coagulum or whole blood which can have a weaker transmissivity. The respective upper gel thresholds can allow the gel to be distinguished from phases such as air which can have an even stronger transmissivity. The aforementioned gel thresholds can lie in a comparatively high two-digit percentage range, with the upper gel threshold being greater in each case than the lower gel threshold.

In accordance with one embodiment, the coagulum phase type can be determined if the first transmissivity lies below a first coagulum threshold and the second transmissivity lies below a second coagulum threshold. This can account for the fact that coagulum can be the phase type with the lowest transmissivity. Therefore, the two coagulum thresholds can typically be the lowest thresholds occurring in each case. In the case of a very low transmissivity, or else in the case where the light of both wavelengths is blocked completely, it can be possible to reliably deduce the coagulum phase type.

In accordance with one embodiment, the whole blood phase type can be determined if the first transmissivity lies above a lower first whole blood threshold and below an upper first whole blood threshold and the second transmissivity lies above a lower second whole blood threshold and below an upper second whole blood threshold. This can account for the fact that although whole blood can be slightly more transmissive than coagulum, it can be less transmissive than gel. Therefore, the aforementioned whole blood thresholds can typically lie between a respective coagulum threshold and a respective lower gel threshold.

Below, some possible embodiments of the method are described that relate to how it can be possible to deduce a mixed state or an unmixed state from identified phases or phase types at different positions. It can be understood that the mentioned embodiments can also be combined with one another as desired such that the state of the sample can be deduced on the basis of as many characteristics as possible. This can increase the reliability. By way of example, an error message can be output in the case of deviating results or, as a precaution, a mixed state can be determined even if only one of the possible embodiments establishes a mixed state.

In accordance with one embodiment, a mixed state can be determined if a gel phase type is determined at a position between a closed or lower end of the sample tube and an upper gel position.

The upper gel position can preferably be the position up to which, in the supplied state of the sample tube, gel typically extends toward the top from the closed or lower end of the sample tube. Expressed differently, it can be the filling height predetermined by the manufacturer. By way of example, it can be specified as a length unit proceeding from the closed or lower end of the sample tube.

As already mentioned above, gel can typically be in the lowermost region of the sample tube in a sample tube prior to centrifugation as it was already filled into the sample tube by the manufacturer of the sample tube and it can initially remain at this position, even if blood is subsequently filled into the sample. Only once the sample is transferred into an unmixed state, for example by centrifugation, the gel can be displaced into a position which can be at a measurable distance from the closed or lower end of the sample tube due to density considerations. In the case of an unmixed sample, i.e., for example, a centrifuged sample, the coagulum which can be the densest material present can typically be arranged between the gel and the closed or lower end of the sample tube. Therefore, a non-centrifuged state can be deduced from the presence of gel at the lowermost end of the sample tube.

In accordance with one embodiment, a mixed state can be determined if a whole blood phase type is determined. This can account for the fact that the whole blood phase type can typically be no longer present in a sample subjected to a proper separation into the individual phases, for example by centrifugation. Rather, the constituents of the whole blood, i.e., in particular, plasma on the one hand and cellular constituents on the other hand, can be separated into phases of the plasma and coagulum phase types. Therefore, a mixed state, i.e., for example, a non-centrifuged sample, can be reliably deduced from the presence of the whole blood phase type.

In accordance with one embodiment, an unmixed state can be determined if at least three solid or liquid phases of different types are determined. This can be based on the fact that a sample in the mixed state, i.e., for example, prior to centrifugation, can normally only have two phases. To the extent that this is a sample tube without gel filled therein, a non-centrifuged sample can have merely one phase, that is to say whole blood. To the extent that the sample tube is a sample tube into which gel was filled, the sample typically can have two phases, that is to say whole blood and, therebelow, gel. A third phase can only be generated by separating the phase of the whole blood phase type into the phases of the plasma and coagulum phase types.

In accordance with one embodiment, if a coagulum phase type is determined, a length of the phase of the coagulum phase type can be determined along the longitudinal direction, proceeding from a closed or lower end of the sample tube, and, furthermore, a length of all solid or liquid phases in the sample tube can be determined, proceeding from the closed or lower end of the sample tube, wherein subsequently a ratio between the length of the coagulum and the length of all solid or liquid phases in the sample tube can be thereupon calculated. An unmixed state can be determined if the ratio lies below a separation threshold. A mixed state can be determined if the ratio lies above the separation threshold.

Here, in accordance with an alternative embodiment, the length of the phase of the gel phase type can be subtracted from the length of all solid or liquid phases.

A length of a phase of the gel phase type, which may likewise be situated in the sample, can typically not be included in the length of the phase of the coagulum phase type.

The above embodiment can account for the fact that whole blood that has been filled-in can separate into two different perceivable phases over time, even without action thereon, i.e., in particular, without centrifugation. This can be due to the known blood sedimentation rate, which can normally proceed at around 20 to 40 mm per hour. This can correspond to the speed with which a phase perceivable as plasma can form above a phase with, compared to the original whole blood, an increased concentration of cellular constituents. In terms of the transmissivity characteristics thereof, this phase can be similar or identical to a coagulum, and so it cannot be reliably distinguished from actual coagulum, which was created by centrifugation.

As a result of the procedure described, the reliability can be increased in the case where the sample was already stored for a relatively long time prior to application of the method. This can be particularly advantageous, particularly if no gel is situated in the sample tube as the distinction by way of the position of gel and coagulum relative to one another is not possible in this case.

The separation threshold typically can lie in the low two-digit percentage range. Only if the determined phase of the coagulum phase type assumes a comparatively small part of the overall extent of all solid or liquid phases, the assumption that the sample was in fact separated on purpose, i.e., for example centrifuged, can be made with sufficient reliability. To the extent that the determined phase of the coagulum phase type can assume a predominant portion of the overall extent of all solid and liquid phases in the sample tube, the assumption that the sample tube was merely stored for a certain amount of time and the determined perceived coagulum is a more dense phase of whole blood can be more likely. In this case, there can initially have to be centrifugation of the sample tube before it can be possible to carry out further analysis steps.

Reference can be made to the fact that the above embodiment, which can offer a certain amount of safety from incorrectly determining the state in the case of samples which were stored for a long time, can be combined particularly advantageously with the embodiment based on the establishment of three different phase types described above.

By way of example, to the extent the three different phase types, of which one phase can have the coagulum phase type, were identified, the procedure described above can render it possible to prevent a sample from being classified as unmixed even though in fact it was merely stored for a relatively long time. The establishment on the basis of the separation threshold can therefore overrule the result of the establishment on the basis of the presence of three phases.

In accordance with one embodiment, if a gel phase type is determined, an unmixed state can be determined if the gel phase is spaced from a closed end of the sample tube by a minimum distance. This can account for the fact that gel, to the extent that it even is in the sample tube, can continue to stay right at the bottom of the sample tube, i.e. it can continue to form the lowest phase, in a non-centrifuged sample tube. A coagulum phase can form below the gel only in the case of active separation, for example by centrifugation, wherein the gel can be removed from the closed end of the sample tube. It can remain in a state further above the coagulum. Therefore, an unmixed state can reliably be deduced from the presence of gel with a minimum spacing, which typically can correspond to the typical extent of coagulum.

In one embodiment, the at least one property of the sample can be determined continuously along the longitudinal direction. In particular, this can mean that a multiplicity of measurement values can be recorded along the longitudinal direction for the property such that the measurement points in the longitudinal direction can be spaced apart by a distance that can be significantly shorter than typical orders of magnitude in which the properties change, for example by way of a transition between two phases. To the extent that a second property can be determined, the same as for the first property can preferably apply to this property. Hence, a particularly reliable establishment of the state of the sample can be achieved.

A device for analyzing samples, for example, blood samples, which can be contained in sample tubes, is also presented. The device can have the following: a property determining device for determining at least one property of the sample at a plurality of different positions along the longitudinal direction of the sample tube and an electronic control device comprising a processor and storage assigned thereto. Instructions can be stored in the storage which, when executed by the processor, can cause the device to carry out a method described above.

In the method carried out by the device, it can be possible to resort to all variants described with reference to the method. Explained advantages can apply correspondingly.

The device can have at least a first light source and a second light source. The first light source can emit light with a first wavelength between 400 nm and 1200 nm during operation and the second light source can emit light with a second wavelength between 1300 nm and 1700 nm during operation. The device can furthermore have one or more detectors for detecting the light emitted by the first light source and for detecting the light emitted by the second light source, in each case after passage through the sample tube across the longitudinal direction at a position along the longitudinal direction. The first and the second light source can be arranged in a displaceable manner in the longitudinal direction of the sample tube.

By use of the above-described light sources and detectors, it can be possible to establish the first transmissivity and the second transmissivity, as described above. For example, the transmissivity of the light with a wavelength between 400 nm and 1200 nm can be the first transmissivity and the transmissivity of the light with a wavelength between 1300 nm and 1700 nm can be the second transmissivity.

For the purposes of detecting the transmissivities, use can either be made of one detector, which can detect the transmitted light in both relevant spectral regions, or use can be two separate detectors.

Either the light sources can be displaced relative to a sample tube at rest or the sample tube can be displaced relative to the light sources at rest. A simultaneous displacement can also be possible.

A laboratory automation system is also presented. The laboratory automation system can have the following: a receiving station for sample tubes, a centrifuge, a first drive for moving sample tubes from the receiving station into the centrifuge, a device described above for analyzing samples, and a second drive for moving sample tubes from the centrifuge into the device for analyzing samples. The control device of the device for analyzing samples can be embodied to perform the described method prior to further analysis steps and not to perform any more analysis steps and preferably output an error message in the case where a mixed state is determined in the process. The described method can advantageously be applied to a largely automated system by way of the laboratory automation system.

The receiving station for sample tubes can be e.g. a conventional sample tube holder. The centrifuge can be e.g. a conventional laboratory centrifuge. The first drive for moving sample tubes from the receiving station into the centrifuge can be e.g. a robot which can remove sample tubes from the receiving station and can insert them into the centrifuge. In the device for analyzing samples, it can be possible to resort to all described embodiments, with explained advantages applying correspondingly. For example, the device for analyzing samples can be the embodiment, described above, with two light sources with different wavelengths. The second drive for moving sample tubes from the centrifuge into the device for analyzing samples can be e.g. a robot which can remove sample tubes from the centrifuge and insert them into the device for analyzing samples. To this end, the device for analyzing samples may, for example, have a similar or identical receiving station as described further above. By way of example, the second drive for moving sample tubes from the centrifuge into the device for analyzing samples and the first drive for moving sample tubes from the receiving station into the centrifuge may be identical. By way of example, this can be the same robot.

In the method to be applied by the laboratory automation system, it can be possible to resort to all embodiments described above. Explained advantages apply correspondingly.

The laboratory automation system can enable a fully automated analysis of samples, with the laboratory automation system also automatically carrying out centrifugation. At the same time, a reliability can be provided which can prevent non-centrifuged samples from being analyzed, wherein these, for example, may occur in the case of a malfunction of one of the drivers for moving samples, for example a robot, or may be triggered by human interventions. The reliability of the overall system can thus be significantly increased.

A user of the laboratory automation system can be made aware of a malfunction by way of an output error message. The user can intervene manually in this case.

The device for analyzing samples can have an analysis apparatus which can establish the desired measurement values to be analyzed, for example blood alcohol content. To this end, the device can have, for example, a driver for removing liquids or solids from the interior of the sample tube and known analysis instruments, e.g. spectroscopic analysis instruments.

Referring initially to FIGS. 1A-D, FIGS. 1A-D show sample tubes 10 with different samples 12 contained therein. The samples 12 can each have one or more phases. The respective phases can have different phase types in the case of a plurality of phases. The explicit designation as "phase" or "phase type" can be generally dispensed with below in order to improve readability. Rather, it can usually only be the respective phase type that is specified below.

Figure 1A:
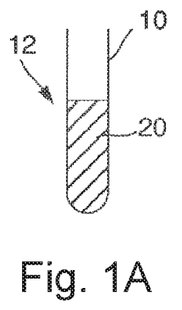
FIGS. 1A-D illustrate a sample tube with different samples according to an embodiment of the present disclosure.

FIG. 1A shows a sample tube 10 with a sample 12 which can consist entirely of whole blood 20. The whole blood 20 can be in a mixed state. This can indicate that the sample 12 in the sample tube 10 was not yet separated, i.e., for example, not yet centrifuged.

Figure 1B:
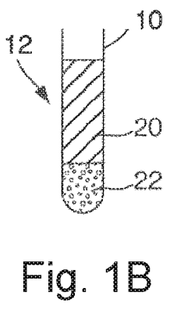

FIG. 1B shows a sample tube 10 with a sample 12 containing both a gel 22 and whole blood 20. Whole blood 20 can be arranged above the gel 22. As already explained above, the gel 22 can already be filled into the sample tube 10 by the manufacturer during the step of manufacturing the sample tube 10 and it can remain at this position, even when blood fills the sample tube 10. Substantial mixing may not occur between the whole blood 20 and the gel 22. Therefore, the sample 12 in FIG. 1B can likewise be a mixed sample, i.e. a still non-centrifuged sample, in which, in contrast to the sample 12 in FIG. 1A, a gel 22 can be additionally present.

Figure 1C:
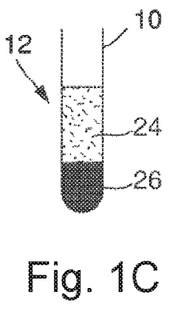

FIG. 1C shows a sample tube 10 with a sample 12 corresponding to the sample 12 already shown in FIG. 1A but can now be in an unmixed state, i.e. centrifuged state. Expressed differently, the sample tube 10 in FIG. 1A was centrifuged in order to obtain the state in FIG. 1C.

What can be identified in FIG. 1C is that coagulum 26 can now be situated at the lower end of the sample tube 10. The coagulum can have a particularly high density. Plasma 24 which can substantially be comprised of the aqueous, non-cellular constituents of the whole blood 20 can be situated above the coagulum 26. That is to say, the whole blood 20 can be separated into the plasma 24 and the coagulum 26.

Figure 1D:
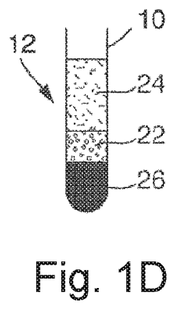

FIG. 1D shows a sample tube 10 with a sample 12 which can have a total of three phases. Coagulum 26 can be situated at the lower end. A gel 22 can be situated immediately thereover. Plasma 24 can be situated once again thereover.

The sample 12 in FIG. 1D can correspond to the sample 12 from FIG. 1B in an unmixed, i.e. centrifuged state. Expressed differently, the sample tube 10 from FIG. 1B can be centrifuged in order to obtain the state depicted in FIG. 1D. Like in the transition from the state depicted in FIG. 1A to the state depicted in FIG. 1C, the whole blood 20 can be separated into the coagulum 26 and plasma 24 during centrifuging in the transition from the state depicted in FIG. 1B to the state depicted in FIG. 1D. Here too, the coagulum 26 can include the cellular constituents, whereas the plasma 24 can include the aqueous, non-cellular constituents. Due to the density thereof, the gel 22 can arrange itself between the coagulum 26 and the plasma 24.

It should be noted that, in the above description of FIGS. 1A to 1D, a phase of the air phase type may not be considered in any more detail in each case. The air can be situated above the aqueous and liquid phases in the sample tube 10 in each case. Normally, the air phase type may not play any role for carrying out the method since the presence of air does not indicate either a mixed or an unmixed state.

Figure 2:
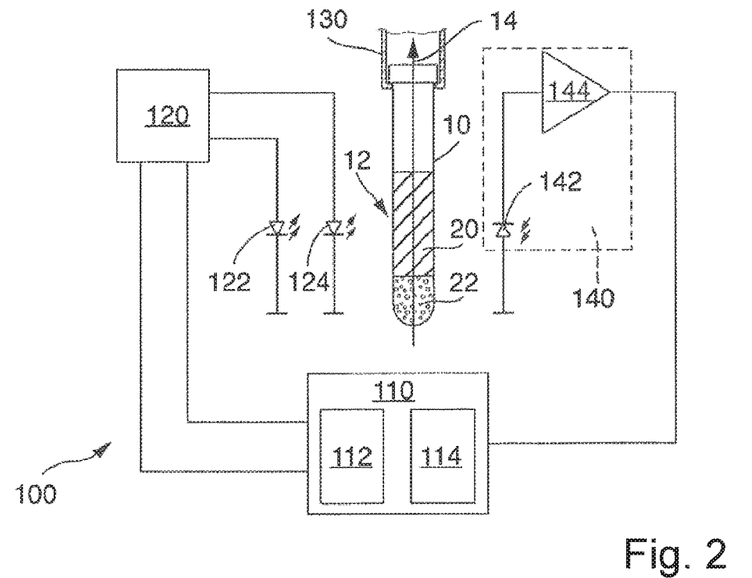
FIG. 2 illustrates a device for analyzing samples according to an embodiment of the present disclosure.

FIG. 2 shows a device 100 for analyzing samples. Situated in the device 100 can be a sample tube 10 with a sample 12 contained therein. As can likewise be identified in FIG. 2, the sample tube 10 can have a longitudinal direction 14, with the sample tube 10, over the extent thereof along the longitudinal direction 14, having a radial symmetric embodiment in respect of the longitudinal direction 14.

The device 100 can have a microcontroller 110 with a light source actuation unit 112 and a computer unit 114. The light source actuation unit 112 can be connected to a driver 120 which, in turn, can be connected to a first light-emitting diode 122 and a second light-emitting diode 124. The light source actuation unit 112 can output signals to the driver 120, whereupon the driver 120 can switch the two light-emitting diodes 122, 124 on and off, as wanted by the light source actuation unit 112.

The first light-emitting diode 122 can emit light with a first wavelength of 980 nm during operation. Alternatively, use can, for example, also be made of 940 nm. The second light-emitting diode 124 can emit light with a second wavelength of 1550 nm during operation. Both the light-emitting diodes 122, 124 can be arranged directly next to the sample tube 10 and the light thereof can be radiated laterally into the sample tube 10 in such a way perpendicular to the longitudinal direction 14 that the light can pass through approximately the center point of the circular sample tube cross section.

A light receiver 140 can be arranged opposite to the light-emitting diodes 122, 124 in respect of the sample tube 10. The light receiver can have a sensor 142 and an operational amplifier 144. In one embodiment, the sensor 142 can be an InGaAs sensor which can have the advantageous property that it can detect light with a wavelength above approximately 850 nm. The operational amplifier 144 can process the signals obtained by the sensor 142 and forward the signals to the microcontroller 110. This can make it possible to measure an intensity of the light emerging from the sample tube 10 and hence to determine a transmissivity or a transmissivity ratio or intensity ratio between the first and the second wavelength.

The sample tube 10 can be received in the sample holder 130 which can be displaceable along the longitudinal direction 14 of the sample tube 10, i.e. both upward and downward. Using this, the transmissivity of the light emitted by at least one of the light-emitting diodes 122, 124 through the sample tube 10 with the sample 12 contained therein can be measured at a multiplicity of positions along the longitudinal direction 14, that is to say practically continuously along the longitudinal direction 14.

The computer unit 114 of the microcontroller 110 can be embodied to carry out the method. To this end, the sample tube 10 can be displaced along the longitudinal direction 14 thereof from top to bottom by the sample holder 130 in such a way that it can be measured over a substantial part of the extent thereof along the longitudinal direction 14 by way of the light-emitting diodes 122, 124 and the light receiver 140. In one embodiment, this can be understood to mean that the first light-emitting diode 122 and then the second light-emitting diode 124 can alternately be switched-on at each position. A light intensity or a transmissivity, i.e. a passage of light through the sample tube 10 with the sample 12 contained therein, can be determined in each case. It can be understood that the sequence of switching-on the two light-emitting diodes 122, 124 can also be interchanged. Likewise, the sample tube 10 can also be displaced from bottom to top.

In this case, respective measurement points can lie very close together along the longitudinal direction 14, meaning that they can be smaller than a typical order of magnitude over which the conditions within the interior of the sample tube 10 change.

By way of the above-described procedure, the microcontroller 110 can obtain two measurement curves which can specify the transmissivity at the first wavelength and the second wavelength at each position along the longitudinal direction 14 of the sample tube 10. After this, the microcontroller 110 can determine whether the sample 12 is in an unmixed or mixed state, i.e., typically, in a centrifuged or non-centrifuged state. To this end, use can be made of the thresholds described below with reference to FIGS. 3A-B.

Figure 3A:
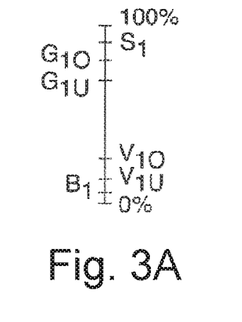
FIGS. 3A-B illustrate schematically typical thresholds according to an embodiment of the present disclosure.
Figure 3B:
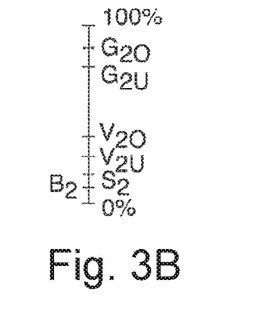

FIGS. 3A-B schematically show typical thresholds for determining respective phase types. Here, FIG. 3A shows the thresholds in relation to the first wavelength, whereas FIG. 3B shows the thresholds in relation to the second wavelength.

The two respective lowest thresholds can be the first coagulum threshold $B_1$ and the second coagulum threshold $B_2$. To the extent that the transmissivity can lie below these thresholds in each case, coagulum can be assumed.

In FIG. 3A, a lower first whole blood threshold $V_{1U}$ and an upper first whole blood threshold $V_{1O}$ can be situated above the first coagulum threshold $B_1$. In FIG. 3Bb, a lower second whole blood threshold $V_{2U}$ and an upper second whole blood threshold $V_{2O}$ can be situated above the second coagulum threshold $B_2$, wherein however, in contrast to FIG. 3A, a second plasma threshold $S_2$ can be arranged between the second coagulum threshold $B_2$ and the lower second whole blood threshold $V_{2U}$.

A whole blood phase type can be assumed provided that the first transmissivity can be between the two first whole blood thresholds $V_{1U}$, $V_{1O}$ and the second transmissivity can be between the two second whole blood thresholds $V_{2U}$, $V_{2O}$.

Gel thresholds can be situated above the respective upper whole blood threshold $V_{1O}$, $V_{2O}$ in each case. In the case of FIG. 3A, these can be a lower first gel threshold $G_{1U}$ and an upper first gel threshold $G_{1O}$. In the case of FIG. 3B, these can be a lower second gel threshold $G_{1U}$ and an upper second gel threshold $G_{2O}$. A gel phase type can be assumed provided that the first transmissivity can be between the two first gel thresholds $G_{1U}$, $G_{1O}$ and the second transmissivity can be between the two second gel thresholds $G_{1U}$, $G_{2O}$.

FIG. 3A moreover shows that there still is a first plasma threshold $S_1$ above the upper first gel threshold $G_{1O}$. A plasma phase type can be assumed provided that the first transmissivity can be above the first plasma threshold $S_1$ and the second transmissivity can be below the second plasma threshold $S_2$.

After determining the respective phases at the respective positions, the microcontroller 110 can determine whether the sample 12 is in a mixed or unmixed state. Here, the following procedure can be carried out:

To the extent that a coagulum 26 phase type is determined, there can be establishment of a length of the coagulum 26 and also of a length of all solid and liquid phases 20, 22, 24, 26 in the sample tube 10. Subsequently, the ratio of the length of the coagulum 20 to the overall length of all solid and liquid phases 20, 22, 24, 26 can be determined. A mixed state can be determined to the extent that this ratio can lie above the separation threshold. An unmixed state can be determined to the extent that the ratio can lie below the separation threshold. This can account for the phenomenon, described above, of natural blood sedimentation and can prevent a sample which was merely separated in part due to blood sedimentation from being classified as being in an unmixed state.

To the extent that the gel 22 phase type is determined, there can be further determination as to whether a phase of the gel 22 phase type is situated directly at the lower end, i.e. adjacent to the closed end of the sample tube 10, or at a certain minimum distance from the lower end of the sample tube 10. A mixed state can be determined in the first case. An unmixed state can be determined in the second case.

If the two described establishment methods supply different results, an error message can be output. If both establishment methods establish an unmixed state or if the first establishment method establishes an unmixed state and the second establishment method is not applicable due to the lack of presence of gel 22, the sample 12 situated in the sample tube 10 can be determined to have been clearly centrifuged and can be analyzed. If the two described establishment methods result in a mixed state or the first described establishment method results in a mixed state and the second establishment method is not applicable due to the lack of presence of a gel 22, the sample 12 situated in the sample tube 10 can be determined not to have been centrifuged and is unable to be analyzed. The user can be informed of this case.

Figure 4:
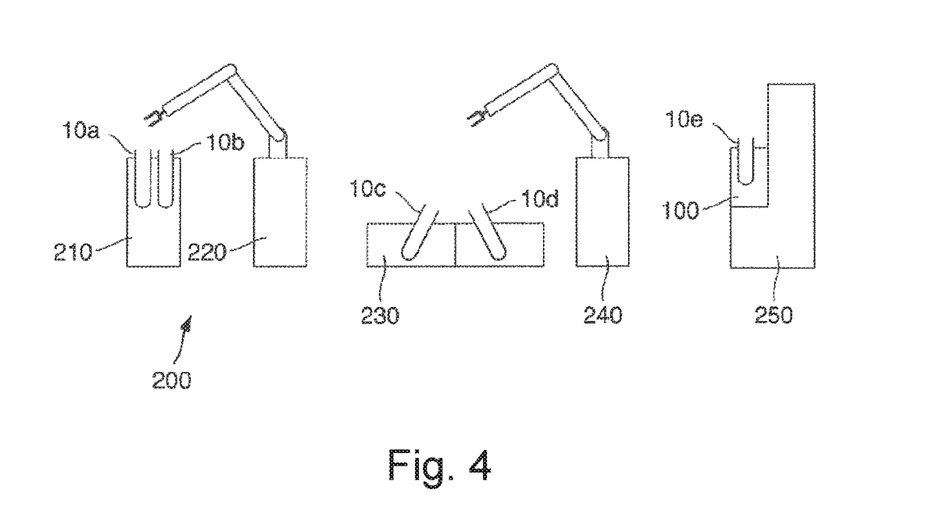
FIG. 4 illustrates a laboratory automation system according to an embodiment of the present disclosure.

FIG. 4 shows a laboratory automation system 200. The laboratory automation system 200 can have a receiving station in the form of a sample stand 210, in which two sample tubes 10a, 10b can be situated. Sample tubes 10, 10a, 10b to be analyzed can be introduced manually into the sample stand 210.

The laboratory automation system furthermore can have a centrifuge 230, into which two sample tubes 10c, 10d have been introduced. Samples, which can be situated in the sample tubes 10, 10c, 10d, can be separated by centrifugal force by the centrifuge 230, which can be a conventional, known laboratory centrifuge.

A first robot 220, which can remove the sample tubes 10a, 10b from the sample stand 210 and insert them into the centrifuge 230, can be situated between the sample stand 210 and the centrifuge 230. Therefore, the centrifuge 230 can be equipped in a fully automated manner.

The laboratory automation system furthermore can have an analysis instrument 250, which can establish the desired medical data of the sample contained in the respective sample tubes. The analysis instrument 250 can have a device 100 for analyzing samples, as depicted in FIG. 2.

A second robot 240, which can be embodied to remove sample tubes 10, 10c, 10d from the centrifuge 230 and insert them into the device 100 for analyzing samples, can be provided between the centrifuge 230 and the analysis instrument 250. In the present case, a sample tube 10e is shown in the device 100, which sample tube can initially be checked by the device 100 as to whether it was centrifuged and, in the case of a positive result, it can subsequently be analyzed by the latter.

The above-described laboratory automation system 200 can enable complete automation of the analysis, over centrifugation up to the analysis, after insertion of the sample tube 10 with the sample 12 situated therein. The provision of the device 100 for analyzing samples, which can carry out a check prior to the analysis as to whether the samples were in fact centrifuged, can provide additional protection against malfunctions or in the case of possible human interventions. By way of example, a human can directly insert a non-centrifuged sample in a corresponding sample tube into the device 100 because he can desire particularly quick analysis thereof. In this case, the device 100 can identify that the sample had not been centrifuged and decline the analysis.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A method for automated identification of a state of a sample, from a predetermined set of states by a device, wherein the set of states contains an unmixed state and a mixed state and wherein the sample is situated in a sample tube extending along a longitudinal direction, the method comprises:
    determining at least one property of the sample at a plurality of different positions along the longitudinal direction;
    determining at least one phase type of a phase of the sample in the sample tube on the basis of the determined property; and
    determining the state of the sample as a unmixed state or as a mixed state in a manner dependent on the determined phase type, wherein at a respective position a first transmissivity of the sample across the longitudinal direction at a first wavelength is determined as a first property and a second transmissivity of the sample across the longitudinal direction at a second wavelength is determined as a second property during the step of determining at least one property.

2. The method according to claim 1, wherein a plasma phase type is determined if the first transmissivity lies above a first plasma threshold ($S_1$) and the second transmissivity lies below a second plasma threshold ($S_2$).

3. The method according to claim 1, wherein a gel phase type is determined if the first transmissivity lies above a lower first gel threshold ($G_{1U}$) and below an upper first gel threshold ($G_{1O}$) and the second transmissivity lies above a lower second gel threshold ($G_{2U}$) and below an upper second gel threshold ($G_{2O}$).

4. The method according to claim 1, wherein a coagulum phase type is determined if the first transmissivity lies below a first coagulum threshold ($B_1$) and the second transmissivity lies below a second coagulum threshold ($B_2$).

5. The method according to claim 1, wherein a whole blood phase type is determined if the first transmissivity lies above a lower first whole blood threshold ($V_{1U}$) and below an upper first whole blood threshold ($V_{1O}$) and the second transmissivity lies above a lower second whole blood threshold ($V_{2U}$) and below an upper second whole blood threshold ($V_{2O}$).

6. The method according to claim 1, wherein a mixed state is determined if a gel phase type is determined at a position between a closed end of the sample tube and an upper gel position.

7. The method according to claim 1, wherein a mixed state is determined if a whole blood phase type is determined.

8. The method according to claim 1, wherein an unmixed state is determined if at least three solid or liquid phases of different types are determined.

9. The method according to claim 1, wherein, if a coagulum phase type is determined, a length of the phase of the coagulum phase type is determined along the longitudinal direction, proceeding from a closed end of the sample tube, and a length of all solid or liquid phases in the sample tube is determined, proceeding from the closed end of the sample tube, and subsequently a ratio between the length of the phase of the coagulum phase type and the length of all solid or liquid phases in the sample tube is calculated, and wherein an unmixed state is determined if the ratio lies below a separation threshold and wherein a mixed state is determined if the ratio lies above the separation threshold.

10. The method according to claim 1, wherein, if a gel phase type is determined, an unmixed state is determined if a gel phase is spaced from a closed end of the sample tube by a minimum distance.

11. The method according to claim 1, wherein the at least one property of the sample is determined continuously along the longitudinal direction.

12. A device for analyzing samples, contained in sample tubes, the device comprising:
an electronic control device comprising a processor and storage assigned thereto, wherein the processor executes the method of claim 1.

13. The device according to claim 12, further comprises,
at least a first light source, wherein the at least first light source (122) emits light with a first wavelength between 400 nm and 1200 nm during operation;
a second light source, wherein the second light source emits light with a second wavelength between 1300 nm and 1700 nm during operation; and
at least one detector for detecting the light emitted by the first light source and for detecting the light emitted by the second light source, in each case after passage through the sample tube across the longitudinal direction at a position along the longitudinal direction, wherein the first and the second light sources and/or the at least one detector is/are arranged in a displaceable manner in the longitudinal direction of the sample tube.

* * * * *